(12) United States Patent
Pojarliev et al.

(10) Patent No.: US 7,550,626 B2
(45) Date of Patent: Jun. 23, 2009

(54) PROCESS FOR PREPARING RACEMIC ALKYL-5-HALOPENT-4-ENECARBOXYLIC ACIDS OR CARBOXYLIC ESTERS

(75) Inventors: Peter Pojarliev, Vienna (AT); Gerhard Steinbauer, Enns (AT); Christian Burger, Leonding (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 0 days.

(21) Appl. No.: 11/995,553

(22) PCT Filed: Jul. 3, 2006

(86) PCT No.: PCT/EP2006/006438

§ 371 (c)(1),
(2), (4) Date: May 1, 2008

(87) PCT Pub. No.: WO2007/017018

PCT Pub. Date: Feb. 15, 2007

(65) Prior Publication Data

US 2008/0207943 A1    Aug. 28, 2008

(30) Foreign Application Priority Data

Jul. 25, 2005    (EP) ............... A 1240/2005

(51) Int. Cl.
*C07C 69/62*    (2006.01)
*C07C 53/15*    (2006.01)

(52) U.S. Cl. ............ 560/219; 562/598; 562/602

(58) Field of Classification Search ............ None
See application file for complete search history.

(56) References Cited

U.S. PATENT DOCUMENTS 7,232,925 B2 * 6/2007 Mori et al. ............ 560/219
2007/0191630 A1 * 8/2007 Sakaeda et al. ............ 560/219

FOREIGN PATENT DOCUMENTS

WO    2004/052828    9/2005

WO    2006/041062    4/2006

OTHER PUBLICATIONS

International Search Report for PCT/EP2006/006438 mailed Oct. 10, 2006.
Izv. Akad. Nauk Armyan SSR 1960, 13, 259, Chemical Abstract 1961, 55, 20950h.

* cited by examiner

*Primary Examiner*—Karl J Puttlitz
(74) *Attorney, Agent, or Firm*—Nixon & Vanderhye P.C.

(57) ABSTRACT

A process for preparing racemic alkyl-5-halopent-4-enecarboxylic acids and esters thereof of the formula (I), in which R is a $C_1$-$C_6$-alkyl radical, $R_1$ is H or $C_{1-4}$-alkyl and X is chlorine, bromine or iodine, which comprises a) reacting a dialkyl alkylmalonate of the formula (II), in which R is as defined above and $R_2$ is a $C_1$-$C_4$-alkyl radical, in the presence of a metal alkoxide of the formula $MOR_3$, in which M may be Na, K or Li, and $R_3$ is a $C_1$-$C_4$-alkyl radical, and in an organic solvent, with 1,3-dihalopropene to give the corresponding allylated malonate, then b) after full conversion, adding an inorganic salt and a $C_1$-$C_6$ alcohol to the reaction mixture, heating the reaction mixture to reflux temperature, then c) isolating the desired racemic ester of the formula (I) from the reaction mixture by extraction or direct distillation and d) if the racemic acid is the desired end product, hydrolyzing the ester function.

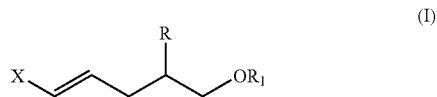

(I)

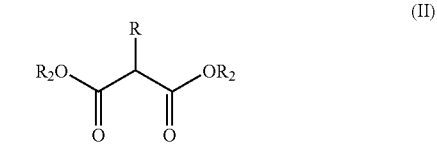

(II)

10 Claims, No Drawings

PROCESS FOR PREPARING RACEMIC ALKYL-5-HALOPENT-4-ENECARBOXYLIC ACIDS OR CARBOXYLIC ESTERS

This application is the U.S. national phase of International Application No. PCT/EP2006/006438 filed Jul. 3, 2006 which designated the U.S. and claims priority to Austria Patent Application No. 1240/2005 filed Jul. 25, 2005, the entire contents of each of which are hereby incorporated by reference.

The present invention relates to a process for preparing racemic alkyl-5-halopent-4-enecarboxylic acids or their esters.

Alkyl-5-halopent-4-enecarboxylic acids and their esters are valuable intermediates for preparing pharmaceuticals, for instance for delta-amino-gamma-hydroxy-omega-arylalkanecarboxamides which have renin-inhibiting properties and can be used as antihypertensives in pharmaceutical formulations.

One example of a preparation variant for alkyl-5-halopent-4-enecarboxylic esters is described in WO 01/09079, according to which the desired esters are obtained by reaction of isovaleric esters with 1,3-dihalo-1-propene in the presence of a strong superbase, for instance lithium diisopropylamide (LDA) and potassium tert-butoxide (KOtBu), in a yield of 84% as the racemate.

A significant disadvantage of this process is the use of the superbase, as a result of which low reaction temperatures (−15° C.) are additionally necessary. Since LDA is additionally prepared from the expensive n-butyllithium, the process cannot be employed on the industrial scale for economic reasons.

J. Agric. Food Chem., 32 (1), p. 85-92 discloses, for example, the preparation of various haloalkenecarboxylic acids, for example the racemic 2-isopropyl-5-chloropent-4-enecarboxylic acids, starting from the corresponding dialkyl isopropylmalonate. The malonate is first alkylated with 1,3-dichloro-1-propene in the presence of sodium hydride, which is followed by a dealkoxycarboxylation, and the ester is then hydrolyzed to the racemic 2-isopropyl-5-chloropent-4-enecarboxylic acid. From an economic and operational point of view, a disadvantage of use on the industrial scale is the use of NaH as a base in the alkylation and DMSO as a solvent in the dealkoxycarboxylation.

According to WO 2004/052828, the process from J. Agric. Food Chem., 32 (1), 1, p. 85-92 is modified easily in relation to some process parameters. The corresponding esters are obtained in a yield of only 75% as the racemate.

It was an object of the present invention to find a process for preparing racemic alkyl-5-halopent4-enecarboxylic acids and esters thereof, which enables the preparation of the desired compounds in higher yields compared to the prior art, and an economically viable and more environmentally compatible process.

The present invention accordingly provides a process for preparing racemic alkyl-5-halopent4-enecarboxylic acids and esters thereof of the formula (I)

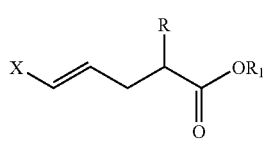
(I)

in which R is a $C_1$-$C_6$-alkyl radical, $R_1$ is H or $C_1$-$C_4$-alkyl and X is chlorine, bromine or iodine, which comprises a) reacting a dialkyl alkylmalonate of the formula (II)

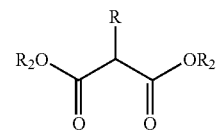

in which R is as defined above and $R_2$ is a $C_1$-$C_4$-alkyl radical, in the presence of a metal alkoxide of the formula $MOR_3$, in which M may be Na, K or Li, and $R_3$ is a $C_1$-$C_4$-alkyl radical, and in an organic solvent, with 1,3-dihalopropene to give the corresponding allylated malonate, then b) after full conversion, adding an inorganic salt and a $C_1$-$C_6$ alcohol to the reaction mixture, heating the reaction mixture to reflux temperature, then c) isolating the desired racemic ester of the formula (I) by extraction or direct distillation and d) if the racemic acid is the desired end product, hydrolyzing the ester function.

The process according to the invention prepares racemic alkyl-5-halopent4-enecarboxylic acids or esters thereof of the formula (I).

In the formula (I), R is a $C_1$-$C_6$-alkyl radical, for instance methyl, ethyl, propyl, isopropyl, n-, iso- and tert-butyl, pentyl and hexyl.

Preference is given to $C_1$-$C_4$-alkyl radicals, particular preference to the isopropyl radical.

$R_1$ is H in the case of the carboxylic acids, and is a $C_1$-$C_4$-alkyl radical, preferably a $C_1$-$C_2$-alkyl radical and more preferably a methyl radical in the case of the esters.

X is chlorine, bromine or iodine, preferably chlorine.

The inventive preparation of the racemic carboxylic acids or esters thereof of the formula (I) proceeds in a plurality of steps.

In the first step a), a dialkyl alkylmalonate of the formula (II) in which R is as defined above and $R_2$ is a $C_1$-$C_4$-alkyl radical is reacted, i.e. allylated, with 1,3-dihalopropene.

Compounds of the formula (II) can be prepared in accordance with the prior art, for example in accordance with WO 2004/052828.

The compounds of the formula (II) are preferably prepared by reacting a corresponding dialkyl malonate of the formula (III)

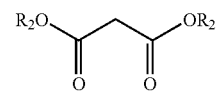

in which $R_2$ is as defined above with an alkyl halide of the formula R—X, where X is bromine, chlorine, iodine and R is as defined above in a suitable solvent in the presence of a metal alkoxide of the formula $MOR_3$ in which M may be Na, K or Li and $R_3$ is a $C_1$-$C_4$-alkyl radical.

The halide is used in an amount of from 0.8 to 1.5 molar equivalents, preferably from 1.0 to 1.1 molar equivalents, based on the malonate of the formula (III). Particular preference is given to bromides.

The metal alkoxide is likewise used in an amount of from 0.8 to 1.5 molar equivalents, preferably from 1.0 to 1.1 molar equivalents, based on the malonate of the formula (III).

Suitable solvents are aprotic solvents, for instance aromatic hydrocarbons (toluene, xylene, benzene, etc.), aliphatic hydrocarbons (hexane, heptane, etc.), polar aprotic solvents such as amides and sulfoxides (DMF, DMA, NMP, DMSO, sulfolane, etc.), ethers (THF, MTBE, etc.).

Preference is given to using DMF.

The compound of the formula (II) is then isolated by extraction. The compound is preferably purified by distillation by means of a column under reduced pressure.

1,3-Dihalopropene is added in an amount of from 0.8 to 1.5 molar equivalents, preferably from 1.0 to 1.1 molar equivalents. Preference is given to using 1,3-dichloropropene.

The reaction is effected in the presence of a metal alkoxide of the formula $MOR_3$ in which M may be Na, K or Li and $R_3$ is a $C_1$-$C_4$-alkyl radical, and in an organic solvent.

The metal alkoxide is used in an amount of from 0.6 to 1.3 molar equivalents, preferably from 0.9 to 1.1 molar equivalents, based on the malonate of the formula (II).

Suitable solvents are aprotic solvents, for instance aromatic hydrocarbons (toluene, xylene, benzene, etc.), aliphatic hydrocarbons (hexane, heptane, etc.), polar aprotic solvents such as amides and sulfoxides (DMF, DMA, NMP, DMSO, sulfolane, etc.), ethers (THF, MTBE, etc.), DMSO etc.

Preference is given to using DMF.

The reaction temperature for step a) is from 40 to 200° C., preferably from 60 to 90° C.

On completion of reaction, in step b) (dealkoxycarboxylation), an inorganic salt is added, for instance LiCl, NaCl, $CaCl_2$, $MgCl_2$, NaBr, LiCN, NaCN, etc., preferably LiCl or $CaCl_2$, and a $C_1$-$C_6$ alcohol, preferably a $C_1$-$C_4$ alcohol, more preferably methanol. The inorganic salt is added in an amount of from 0.1 to 1.5 molar equivalents, preferably from 0.5 to 0.75 molar equivalents, based on the allylated malonate.

The alcohol is added in an amount of from 0.5 to 3.0 molar equivalents, preferably from 0.8 to 1.5 molar equivalents, based on the allylated malonate.

The reaction mixture is then heated at a temperature of from 130 to 180° C. for a certain time, preferably at 140-145° C. in the case of DMF as the solvent.

Subsequently, the racemic ester of the formula (I) is obtained by extraction or direct distillation.

When the appropriate carboxylic acid of the formula (I) is the desired end product, the ester function is hydrolyzed by customary methods, for example by adding NaOH and water and subsequently distilling the alcohol formed. The acid is isolated by extraction.

Starting from the corresponding alkyl malonates, the racemic alkyl-5-halopent4-enecarboxylic acids and their esters are obtained by the process according to the invention in higher yields in comparison to the prior art of up to 98% of theory.

It is particularly advantageous that, in comparison to the prior art, as a result of the addition of alcohol instead of water, significantly smaller amounts of salt are required and there is no vigorous evolution of gas during the dealkoxycarboxylation.

The racemic alkyl-5-halopent4-enecarboxylic acids and their esters prepared in accordance with the invention can then be separated into their antipodes by customary methods (for example enzymatic or classical optical resolution).

EXAMPLE 1

382 g (406 ml) of DMF were initially charged in a Schmizzo and 137 g (141 ml) of 1.0 eq. NaOMe (30% solution in methanol) were added. This mixture was then heated to 60° C. (±3° C.) and 131 g (0.753 mol) of dimethyl isopropylmalonate were metered in within one hour. Subsequently, a methanol/DMF mixture (201 g) was distilled off under pressure (300 mbar to 60 mbar) and a temperature of 60° C.

Thereafter, at 80° C. (±3° C.), 86 g (79 ml, 0.779 mol, 1.03 eq.) of 1,3-dichloropro were metered in within one hour and the reaction mixture was then heated at 80° C. (±3° C.) for two hours.

The reaction mixture was heated to 140° C. and a 25% solution of LiCl (0.6 eq.) in methanol (19 g of LiCl in 58 g of methanol) was metered in within two hours, and the reaction mixture was heated at 140-142° C. for a further 6 hours, in the course of which a portion of the methanol was distilled off and approx. 1.5 mol of gas (mainly $CH_3Cl$ and $CO_2$) formed. The maximum amount of gas in the first half hour was approx. 6 liters.

On completion of reaction, the solvent (DMF) and the excess methanol were distilled off substantially fully under reduced pressure. The remainder was admixed with 200 g of water, 89 g of 34% HCl and 200 g of MTBE, and the phases were separated. The organic phase was washed 1x with 50 g of water and the solvent was removed under reduced pressure. Approx. 140 g of product were obtained, of which approx. 125 g were ester and 13 g the corresponding acid.

To prepare the corresponding acid, the above product was processed further. 140 g of crude product were suspended in 150 g of water and 70 g of 50% NaOH (1.15 eq.) were added. The reaction mixture was initially charged in an autoclave and heated at max. 3 bar and a temperature of 100-110° C. for two hours. On completion of reaction, the methanol formed was distilled off via the top. Thereafter, the mixture was adjusted to pH 1.5 with $H_2SO_4$ (76%) and extracted 2× with 100 g of IPAT each time, and the solvent was removed under reduced pressure. 125-127 g of acid (96% of theory) were obtained as a colorless liquid.

EXAMPLE 2

A reaction vessel was charged with dimethylformamide (406 ml, 382 g) and sodium methoxide (140 ml, 136 g, 753 mmol, a 30% solution in methanol). The reaction mixture was heated to 60° C. Dimethyl isopropylmalonate (127 ml, 131 g, 753 mmol) was metered in within thirty minutes, and methanol was distilled off at a temperature of 69-74° C. and a pressure of 330-50 mbar.

trans-1,3-Dichloropropene (70 ml, 84 g, 753 mmol) was metered in at 80° C. within one hour and the reaction solution was stirred at 80° C. for ninety minutes.

$CaCl_2$ (83.5 g, 753 mmol) was added and the mixture was heated to 140-145° C. Methanol was metered in continuously (a total of 30 ml, 24 g, 742 mmol), in the course of which the reaction temperature was kept at approx. 140-145° C. The suspension is stirred at this temperature for 12 hours, in the course of which gas (mainly $CH_3Cl$ and $CO_2$) formed. The maximum amount of gas in the first half hour was approx. 6 liters.

Dimethylformamide (260 ml, 247 g) was distilled off at 70-80° C. and a pressure of (150-25 mbar). The resulting suspension was cooled to 55° C., and admixed with 250 g of water, 90 g of HCl (a 34% aqueous solution) and 190 g of MTBE.

The phases were separated and the organic phase was washed with 100 g of water. The organic phase thus obtained was worked up as follows:

The organic MTBE phase was concentrated under reduced pressure. The remainder of MTBE was removed by adding 50 g of water and distilling off an MTBE/water mixture.

Water (135 g) and sodium hydroxide solution (75 g, 49 ml, a 50% aqueous solution) were added, and the reaction solution was heated at a pressure of max. 3 bar and 105-110° C. for two hours. On completion of reaction, approx. 60 ml of an MeOH/water mixture were distilled off. Thereafter, water (135 g) was added and adjusted to pH 3.0-4.0 with $H_2SO_4$ (76% aqueous solution). The solution was pressure. 191 g of racemic acid were obtained as brownish liquid (92% of theory).

The organic MTBE phase was extracted with water (25 g) and sodium hydroxide solution (10 g, 50% aqueous solution), and then washed with water (25 g). The combined aqueous phases contained 17 g of rac. acid (13% of theory) which can be esterified with MeOH and catalytic amounts of $H_2SO_4$.

The organic phase was concentrated under reduced pressure and the residue was distilled at 170-171° C. and standard pressure. 113 g of rac. ester were obtained as a colorless liquid (79% of theory).

What is claimed is:

1. A process for preparing racemic alkyl-5-halopent-4-enecarboxylic acids and esters thereof of the formula (I)

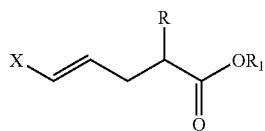

in which R is a $C_1$-$C_6$ alkyl radical, $R_1$ is H or $C_1$-$C_4$-alkyl and X is chlorine, bromine or iodine, which comprises:

a) reacting a dialkyl alkylmalonate of the formula (II)

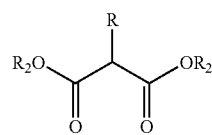

in which R is as defined above and $R_2$ is a C1-C4-alkyl radical, in the presence of a metal alkoxide of the formula $MOR_3$, in which M may be Na, K or Li, and $R_3$ is a $C_1$-$C_4$-alkyl radical, and in an organic solvent, with 1,3-dihalopropene to give the corresponding allylated malonate, then b) after full conversion, adding an inorganic salt and a $C_1$-$C_6$ alcohol to the reaction mixture, heating the reaction mixture to reflux temperature, then c) isolating the desired racemic ester of the formula (I) from the reaction mixture by extraction or direct distillation and d) if the racemic acid is the desired end product, hydrolyzing the ester function.

2. The process as claimed in claim 1, wherein 1,3-dihalopropene is used in step a) in an amount of from 0.8 to 1.5 molar equivalents and the metal alkoxide in an amount of from 0.6 to 1.3 molar equivalents, based in each case on the malonate of the formula (II).

3. The process as claimed in claim 1, wherein the 1,3-dihalopropene used is 1,3-dichloropropene.

4. The process as claimed in claim 1, wherein the inorganic salt used in step b) is a salt from the group of LiCl, $CaCl_2$, $MgCl_2$, NaCl, NaBr, LiCN or NaCN, and the alcohol used is a $C_1$-$C_4$ alcohol.

5. The process as claimed in claim 1, wherein the inorganic salt is used in step b) in an amount of from 0.1 to 1.5 molar equivalents and the alcohol in an amount of from 1.0 to 3.0 molar equivalents, based in each case on the allylated malonate.

6. The process as claimed in claim 1, wherein the dialkyl alkylmalonate of the formula (II) is first prepared by reacting a corresponding dialkyl malonate of the formula (III)

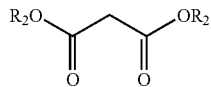

in which $R_2$ is as defined above with an alkyl halide of the formula R-X, where X is bromine, chlorine, iodine and R is as defined above in a suitable solvent in the presence of a metal alkoxide of the formula $MOR_3$ in which M may be Na, K or Li and $R_3$ is a $C_1$-$C_4$-alkyl radical.

7. The process as claimed in claim 6, wherein the halide is used in an amount of from 0.8 to 1.5 molar equivalents and the metal alkoxide in an amount of from 0.8 to 1.5 molar equivalents, based in each case on the malonate of the formula (III).

8. The process as claimed in claim 1, wherein the malonate of the formula (II) is purified by distillation by means of a column under reduced pressure before the reaction with 1,3-dihalopropene.

9. The process as claimed in claim 1, wherein the racemic acids and esters thereof according to formula (I) are obtained in a yield of up to 98% of theory.

10. The process as claimed in claim 1, wherein the racemic acids and esters thereof according to formula (I) are obtained in a yield of 79% up to 98% of theory.

* * * * *